(12) United States Patent
Piletz et al.

(10) Patent No.: US 7,347,984 B2
(45) Date of Patent: Mar. 25, 2008

(54) MAMMALIAN AGMATINASE INHIBITORY SUBSTANCE

(75) Inventors: John E. Piletz, Madison, MS (US); Ming-Ju Huang, Clinton, MS (US); Kenneth S. Lee, Clinton, MS (US)

(73) Assignee: Jackson State University, Jackson, MS (US)

( * ) Notice: Subject to any disclaimer, the term of this patent is extended or adjusted under 35 U.S.C. 154(b) by 614 days.

(21) Appl. No.: 10/818,249

(22) Filed: Apr. 5, 2004

(65) Prior Publication Data

US 2005/0220707 A1    Oct. 6, 2005

(51) Int. Cl.
*A61K 49/00* (2006.01)

(52) U.S. Cl. ..................... 424/9.1; 424/1.11; 424/1.65; 514/157; 514/183

(58) Field of Classification Search ............... 424/1.11, 424/1.65, 9.1, 9.2; 540/1; 544/1, 224; 514/66, 514/70, 156, 157, 183, 188, 218
See application file for complete search history.

(56) References Cited

OTHER PUBLICATIONS

Dox et al, The Harper Collins Illustrated Medical Dictionary, 1993, pp. 125, 126, 133, 152, 227, 308, 348, 355, 356, and 454.*

* cited by examiner

*Primary Examiner*—Dameron L. Jones
(74) *Attorney, Agent, or Firm*—Howrey LLP

(57) ABSTRACT

The present invention provides for methods and compounds for treating brain trauma and disorders such as: ischemia, stroke, neurodegenerative disorders, opioid addiction, idiopathic pain, epilepsy, and depression. More specifically, the invention provides methods for designing and identifying inhibitors of mammalian agmatinase and for compounds identified by these methods.

3 Claims, 10 Drawing Sheets

Agmatine Sulfate

Amino Guanidine

Aminoguanidine hemisulfate: $NH_2NHC(=NH)NH_2 \cdot 1/2H_2CO_3$

Arcaine Sulfate 1,4-Diguanidinobutane sulfate salt: $NH_2C(=NH)NH(CH_2)_4NHC(=NH)NH_2 \cdot H_2SO_4$ 3-Aminopropylguanidine: $C_4H_{14}N_4O_4S$ Trans-4-Aminocyclohexyl guanidine: $C_7H_{18}N_4O_4S$ Alpha-Vinylarginine: $C_8H_{16}N_4O_2$

CS51: $C_{16}H_{24}N_4O_3$

R74: $C_8H_{20}Cl_2N_4$

TRV187: $C_{10}H_{24}N_4$

TRV162: $C_8H_{20}N_4$

G3: $C_{11}H_{25}N_4O_3S$

RO5: $C_{13}H_{29}N_4O_3S$

Bis (3-(N-Iminomethyl)-aminopropyl)amine: $C_7H_{19}N_5$

7-Nitroindazole: $C_7H_5N_3O_2$ where R$_1$: -NH$_2$ or -H
R$_2$: -CH$_3$ or -H
R$_3$: -CH$_3$ or -H
R$_4$: -CH$_3$ or -H
R$_5$: -CH$_3$ or -H

MAMMALIAN AGMATINASE INHIBITORY SUBSTANCE

FIELD OF THE INVENTION

The invention relates to compounds and methods for treating brain trauma and disorders such as: ischemia, stroke, neurodegenerative disorders, opioid addiction, idiopathic pain, epilepsy, and depression. More specifically, the invention is drawn to methods for designing and identifying inhibitors of mammalian agmatinase and to compounds identified by these methods.

BACKGROUND OF THE INVENTION

Agmatine is an endogenous amine and four carbon guanidine cation that is synthesized in the brain following decarboxylation of L-arginine by arginine decarboxylase (ADC: EC 4.1.1.19 (Li et al., 1994). Recent evidence suggests that brain agmatine is more than a mere metabolic intermediate in a pathway leading to polyamine synthesis (Reis and Regunathan, 2000). For instance, animal studies have revealed agmatine's beneficial effects for treating idiopathic pain (Fairbanks et al., 2000), convulsions (Demehri et al., 2003), and stress-related behaviors (Zomkowski et al., 2002 and Lavinsky et al., 2003).

Additionally, studies have indicated that exogenously-administered agmatine undergoes complex interactions with morphine in vivo to: enhance the analgesic effect of (Kolesnikov et al., 1996); block tolerance to and substance dependence on (Li et al. 1999); and attenuate the symptoms caused by withdrawal from morphine (Aricoioglu-Kartal et al., 1997). It has also been shown that agmatine is neuroprotective if given during the early stages of ischemic brain injury (Gilad et al., 1996).

Although originally identified in the brain as an endogenous neurotransmitter that was bound by imidazoline receptors (Li et al., 1994), agmatine's effects have been primarily ascribed to inhibition of nitric oxide synthase (NOS) (Demady et al., 2001) or blockage of glutamate NMDA receptor channels and other ligand-gated cationic channels (Yang et al., 1999).

Existing technology focuses on the use of agmatine itself or the identification of proteins related to, but distinct from agmatinase. For example, U.S. Pat. No. 6,642,039 B1 describes the identification of a human arginase, and polynucleotides encoding the agmatinase-like arginase.

U.S. Pat. No. 6,544,541 B1 describes the use of various eukaryotic mono(ADP-ribosyl)ation transferases (ADPRT) decoy substrates to treat or prevent proliferative disorders, such as restenosis. Included among these decoy substrates is agmatine.

U.S. Pat. No. 6,150,419 describes the use of agmatine as a treatment for neuropathic pain.

U.S. Pat. No. 5,574,059 describes methods for treating disorders mediated by vascular smooth muscle cell proliferation using antiproliferative compounds. Agmatine is listed as among those compounds useful as part of the described treatments.

Thus, there exists a need for compounds that prolong the availability of agmatine. Agmatinase is believed to be the rate-limiting enzyme responsible for regulating the half-life of agmatine in the brain (Sastre et al., 1996). Accordingly, there is a need for compounds that selectively inhibit this enzyme.

SUMMARY OF THE INVENTION

The instant invention provides efficient and effective methods for identifying compounds that selectively inhibit mammalian agmatinase. The invention also provides compounds identified through the use of these methods. Finally, the invention provides for methods of treating brain trauma, neurodegenerative disease, and other maladies using the identified compounds.

One embodiment of the invention provides for a method of determining whether a compound will selectively inhibit agmatinase. One aspect of this embodiment of the invention provides a method that comprises (a) providing or selecting a compound of interest; (b) performing quantitative structure-activity (QSAR) related analysis on the compound; (c) comparing the results of these QSAR analyses for the provided compound with QSAR values for compounds having varying activities on agmatinase, nitric oxide synthases (NOS), arginine decarboxylases (ADC), and NDMA receptor binding; (d) determining whether the QSAR values of the provided compound correspond to a compound that effectively inhibits agmatinase, but does not inhibit ADC, NOS, or binding to NDMA receptors.

In a preferred aspect of the invention the agmatinase is mammalian, specifically agmatine ureohydrolase.

Other embodiments of the invention provide methods for reducing agmatinase activity in an animal comprising administering compounds identified by any of the methods disclosed herein. Such compounds include, but are not limited to one or more of the following: piperazinecarboxamidine, piperidinecarboxamidine, (2S,3S)-2,3-dimethylpiperazinecarboxamidine, (2S)-2-methylpiperazinecarboxamidine, and (4R)-4-aminopiperazinecarboxamidine (see also FIG. 3).

Another embodiment of the invention provide for the use of one of an agmatinase inhibitory compound, identified according to the methods disclosed herein, to treat, ameliorate, or prevent one or more of the following in a patient: ischemia, stroke, neurodegenerative disorders, opioid addiction, idiopathic pain, epilepsy, and depression. In a particularly preferred aspect of this embodiment of the invention the compound used to treat the malady or maladies is selected from one or more compounds selected from the group consisting having the following structures:

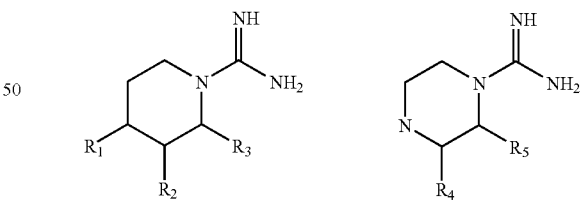

where $R_1$ is either —$NH_2$ or —H and where $R_2$, $R_3$, $R_4$, and $R_5$ are either —$CH_3$ or —H.

Another embodiment of the current invention provides a method for evaluating whether a compound is likely to be an effective agmatinase inhibitor, comprising: (a) selected one or more compounds that are chemically similar to agmatine, but distinct from agmatine with respect to modifications in the guanidine moiety. In one particularly preferred aspect of this embodiment, the chemical similarity is determined by evaluation of the general stereochemistry and/or structure of the compound. Next, analyzing each of the compounds for its inhibitory properties in a series of in vitro assays comprising an agmatinase enzyme activity assay, an arginine decarboxylase (ADC) enzyme activity, an epithelial nitrogen oxide synthase (NOS) assay, an inducible NOS, assay, an neuronal NOS enzyme activity assay, and an NMDA receptor binding activity assay. Next, (c) determining by computer-modeling the optimal chemical properties for each of the compounds using quantitative structure-activity relationship analysis. Next, (d) tabulating and correlating the obtained biochemical inhibition assay data with those chemical properties, determined by computer modeling analysis, for each of the compounds to determine an agmatinase inhibition profile for each compound, and, finally (e) determining whether the tested compound is likely to be useful as an in vivo agmatinase inhibitor by comparing its agmatinase inhibition profile with the profiles of compounds with known effects on agmatinase inhibition.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

| FIG. | Description |
|---|---|
| 1 | Chemical formulas and structures for 14 compounds used in assays to help identify those attributes necessary for an agmatinase inhibitor. |
| 2 | Shows the generic molecular structure and current numbering system for the tested analogs and for analogs predicted to be agmatinase inhibitors. |
| 3 | Compounds predicted to be agmatinase inhibitors |
| 4 | Shows the calculated versus experimental values for remaining activity percentage of rat agmatinase for the 12 compounds tested. See Table 1. |
| 5 | Shows the calculated versus experimental values for remaining activity percentage of rat nNOS for the 13 compounds tested. See Table 2. |
| 6 | Shows the calculated versus experimental values for remaining activity percentage of rat iNOS for the 13 compounds tested. See Table 2. |
| 7 | Shows the calculated versus experimental values for remaining activity percentage of rat eNOS for the 13 compounds tested. See Table 2. |
| 8 | Shows the calculated versus experimental values for remaining binding activity of rat NMDA receptor for the 13 compounds tested. See Table 3. |

Definitions

Figure 1A:
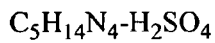
Figure 1A:
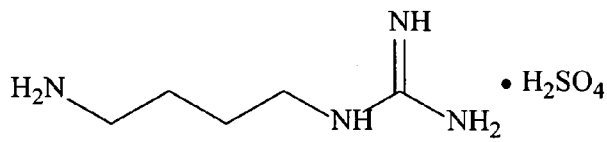
Figure 1A:
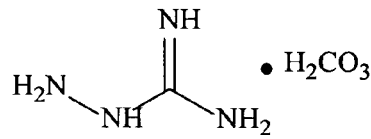
Figure 1A:
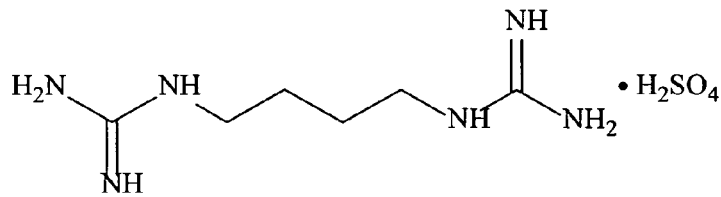
Figure 1A:
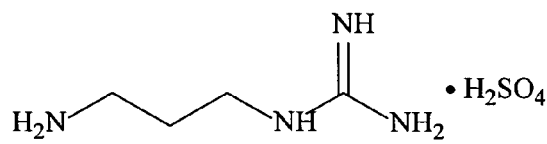
Figure 1B:
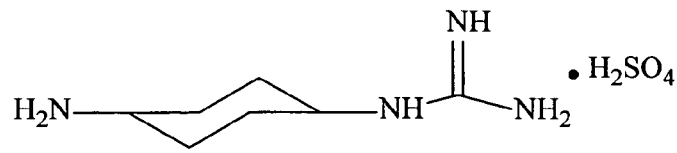
Figure 1B:
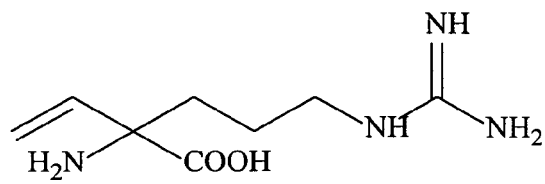
Figure 1B:
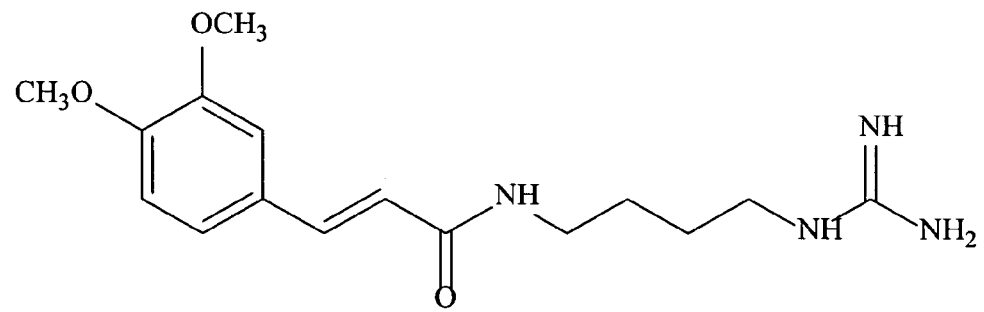
Figure 1B:
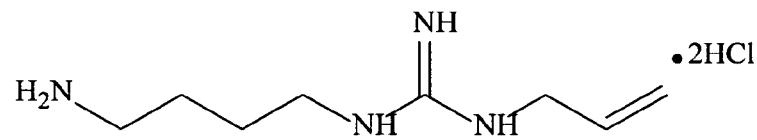
Figure 1C:
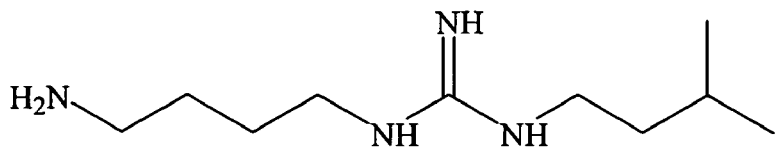
Figure 1C:
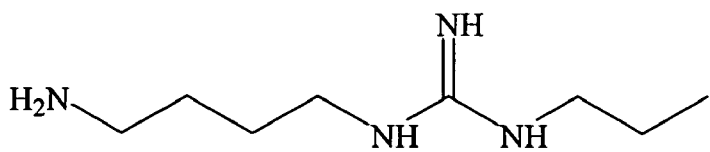
Figure 1C:
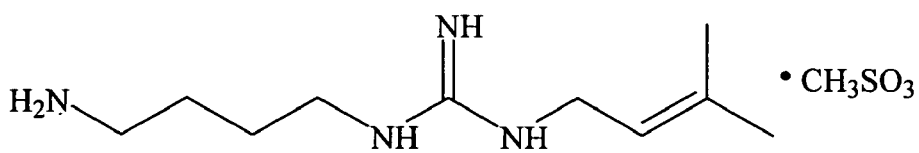
Figure 1C:
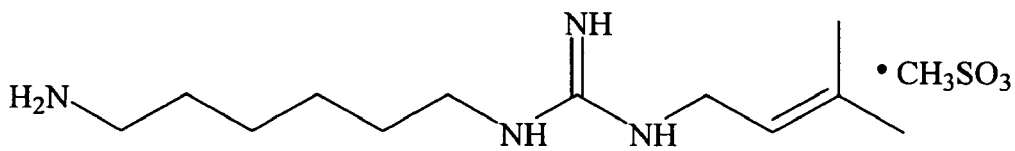
Figure 1C:
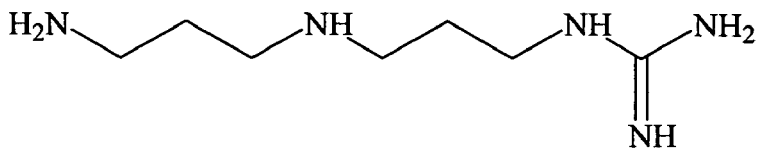
Figure 1C:
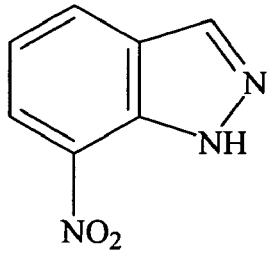

The following definitions are provided in order to aid those skilled in the art in understanding the detailed description of the present invention.

As used herein the term QSAR (quantitative structure-activity relationships) is preferably used to refer to a mathematical relationship showing how a molecule's inhibitory effect (against enzymatic activity or receptor binding) is related to a linear combination of selected molecular properties.

ILLUSTRATIVE EMBODIMENTS OF THE INVENTION

The instant invention provides methods for a rational drug design and for identifying compounds useful for the inhibition of agmatinase. A preferred embodiment of the invention provides methods for identifying inhibitors of mammalian agmatinases (particularly mammalian agmatine ureohydrolase). Also provided are specific compounds designed and prepared using the methods disclosed herein.

As noted above, there is abundant evidence that selective inhibitors of brain agmatinase will be of therapeutic value for treating the following brain maladies: brain trauma including ischemia and stroke, neurodegenerative disorders, opioid addiction, idiopathic pain, epilepsy, and depression.

Agmatine (decarboxylated arginine) was first discovered to exist in mammalian brain about ten years ago. Moreover, the enzyme that is believed to primarily controls its metabolic turnover, agmatinase, was first cloned in 2001. Agmatinase is believed to be the key enzyme for regulating the biological half-life of agmatine in the central nervous system. While the importance of these agmatine and agmatinase as therapeutic targets is still unfolding, all evidence indicates that they play critical roles in a number of important physiological responses. Exogenously-injected agmatine is now recognized as being neuroprotective, especially with respect to brain injuries that cause glutamate and nitric oxide to be overproduced.

Furthermore, animal studies have also shown that exogenously-applied agmatine provides an efficacious treatment for idiopathic pain, convulsions, and stress-mediated behaviors. Exogenously-applied agmatine has also been shown to provide beneficial effects in the treatment and/or prevention of drugs abuse. For instance, agmatine enhances the analgesia of morphine, blocks tolerance to and dependence on morphine, and attenuates the debilitating symptoms associated with from morphine withdrawal.

In view of all of these factors, it is clear that selective drugs capable of prolonging the normally short half-life of agmatine in the brain, will be advantageous for treating brain trauma, idiopathic pain, convulsions, depression, drug abuse and/or other neuropathies.

Thus, this present invention is particularly useful in the area of medicinal pharmaceutics as it provides a surprisingly powerful and effective means for identifying those compounds that are especially potent inhibitors of agmatinases. The disclosed methods provide a cost and time saving mechanism for identifying desirable compounds for use directly as drugs or for use as lead compounds to develop even more effective drugs. As such, the disclosed methods provide an invaluable savings of time, energy, and resources for those seeking to develop effective regimens for the inhibition of agmatinase.

To meet this goal, one embodiment of the instant invention provides a strategy for methods of identifying inhibitor(s) of the brain enzyme that plays the key role in regulating agmatine turnover, agmatinase.

Using the methods described herein, the rank-order of potencies for 11 derivatives of agmatine (having alterations of the guanidine moiety), plus three other compounds with are structural similarity to agmatine, for a total of 14 test compounds. The two compounds that showed the best activity for inhibiting agmatinase were synthesized at Jackson State University by the inventors (namely 3-aminopropylguanidine and trans-4-aminocyclohexyl guanidine). All 14 compounds were tested in vitro for their inhibitory activities against rat agmatinase, using a published assay (see the examples). The same compounds were also tested in five other enzymatic and receptor assays which compose the predicted sites of action of unwanted effects. Thus, one aspect of this embodiment of the invention provide for a method comprising the use of a unique combination of six assays in order to determine the potential ability of a compound to specifically inhibit agmatinase.

From our biochemical dataset, an optimized equation for agmatinase inhibition was thus discovered based on computer-assisted quantitative structure activity relationships (QSAR). This equation has its basis in the geometric and electronic descriptors of the carbons, nitrogens and hydrogens in the guanidine moiety of the test compounds. Using this equation, the potential of new compounds can be evaluated to determine their use as agmatinase inhibitors. Furthermore, according to another aspect of this embodiment of the invention the equation may be used to design any number of new compounds and/or compound classes that possess chemical selectivity as agmatinase inhibitors.

Figure 3:
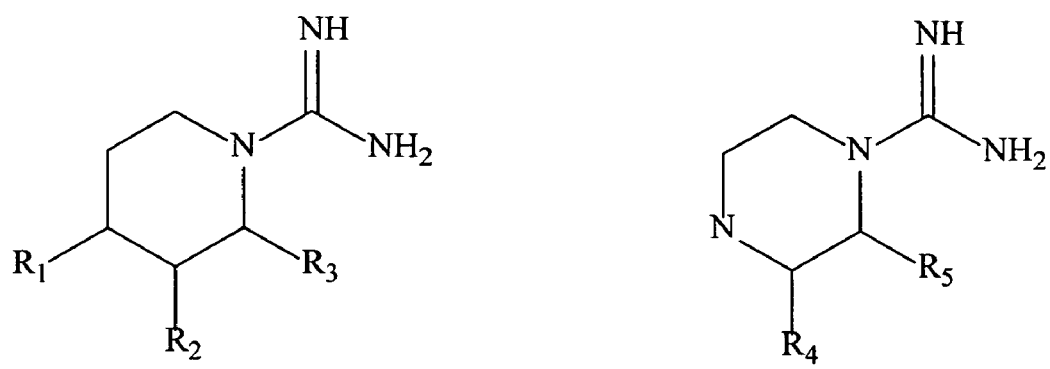

By way of non-limiting example compounds having the general formulas provided in FIG. 3 have been identified as agmatinase inhibitors using this methods of this embodiment of the invention, as described herein. One of ordinary skill in the art will appreciate that the currently described methods may be used to identify many other compounds or compound classes that have anti-agmatinase activity.

While the anti-agmatinase compounds tested to provide the results reported herein are not newly identified organic molecules, their activity against agmatinase was first identified by the inventors and reported herein. Moreover, it is well within ability of the those of ordinary skill in the art, to synthesize and further test agmatinase inhibitors identified by the methods provided herein. One of the remarkable benefits of the methods provided herein is that they predict, with great specificity those compounds or classes of compounds that are most promising and worthy of screening.

In various embodiments the instant invention methods for identifying compounds that are suitable for use as agmatinase inhibitors. Also provided are methods for determining the probability that a particular compound will be effective as an agmatinase inhibitor.

One aspect of this embodiment of the invention provides an improved method for evaluating whether a compound is likely to be an effective agmatinase inhibitor. One particularly preferred aspect of the invention provides for a methods of analyzing the likely effectiveness of a compound for use an agmatinase inhibitor, the method comprising:
(a) obtaining a series of chemically related compounds of roughly the same size/shape/stereochemistry as agmatine, but having modifications, especially in the guanidine moiety;
(b) analyzing each of the compounds for its inhibitory properties in the described battery of 6 in vitro biochemical assays including effect on agmatinase enzyme activity, ADC enzyme activity, eNOS, iNOS, and nNOS enzyme activity, and NMDA receptor binding activity (see example 1);
(c) determining by computer-modeling the optimal chemical parameters/characteristics for each of the compounds as would be expected in aqueous salt solution, and;
(d) tabulating and correlating the obtained biochemical inhibition data with those optimal chemical parameters, determined by computer modeling analysis, for all the compounds in a computer; and,
(e) determining whether the tested compound is likely to be useful as an in vivo agmatinase inhibitor.

Furthermore, as additional and/or new compounds become available, they can be similarly analyzed using steps "(a)" to "(c)", and the new data are added to step "(d)" to strengthen and the precision and accuracy of the method. Those of ordinary skill in the art will appreciate that the accuracy and precision of this method improves as more and more compounds are analyzed. Accordingly, the more compounds that are analyzed using this method, the more precise and accurate the results. Thus, more and more specific and effective agmatinase inhibitor compounds, that optimize the agmatinase equation and minimize the 5 other equations, are identified as more compounds are entered into the database.

Other embodiments of the invention provide for methods of reducing agmatinase activity in an animal by administering an effective amount of one or a combination of two or more compounds whose structure is provided in FIG. 3.

Other embodiments of the invention provide for methods of treating, preventing, or ameliorating maladies including ischemia, stroke, neurodegenerative disorders, opioid addiction, idiopathic pain, epilepsy, and/or depression using one or a combination of two or more compounds whose structure is provided in FIG. 3.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Identification of a Agmatine Specific Inhibitors

Materials and Methods

Agmatine sulfate, aminoguanidine, arcaine sulfate, and 7-nitroindazole were purchased from Sigma Chemical Co. (St. Louis, Mo.). Other agmatine analogues were obtained from a variety of sources. A racemic mixture of alpha-vinylargine was synthesized according to the method of Pederson et al. (1993). Compounds CS51, R74, TRV187, TRV162, G3, and RO5 (see FIG. 1) were obtained from and produced using the methods of Carmignani et al. (2001). The synthesis of 3-aminopropylguanidine and trans-4-aminocyclohexylguanidine were synthesized by adding an aqueous solution of cyanamide drop-wise to a boiling solution of 1,3-diaminopropane or trans-1,4-diaminocyclohexane in a concentrated hydrochloric solution. The mixture was refluxed for 1 hour and then an aqueous solution of NaOH was added. The white precipitate was isolated and an $^1$H NMR spectrum was obtained to confirm the structures. The synthesis of Bis(3-(N-aminomethyl)-aminopropyl)amine is the same as described for 3-aminopropylguanidine and trans-4-aminocyclohexylguanidine except that it uses N-(3-aminopropyl)-1,3-propyldiamine instead of 1,3-diaminopropane or trans-1,4-diaminocyclohexane.

Measurement of Nitric Oxide Synthase (NOS) Activity

NOS activity was measured by monitoring the conversion of [$^3$H]arginine to [$^3$H]citrulline (Bret et al. 1990) using three commercially available isoforms of rat NOS: nNOS (neuronal NOS) (602 units/ml, 14.9 mg/ml), iNOS (inducible NOS) (249.7 units/ml, 21.1 mg/ml), and eNOS (epithelial NOS) (30 units/ml, 14.6 mg/ml) (Cayman, Ann Arbor, Mich.). Neuronal NOS and iNOS were diluted 1:10, while eNOS was used directly without dilution. Unless otherwise indicated, each tube was incubated at 37° C. for 60 minutes.

Assay buffer contained 50 mM Tris-HCl, pH7.4, 2 mM CaCl$_2$, 1 mM NADPH, 10 mM BH$_4$, 5 mM FAD, 5 mM FMN, and 10 mg/ml calmodulin plus radioactive precursor. After incubation, the assay reaction was halted by addition of 400 µl of buffer containing 5 mM EDTA and 50 mM HEPES. Equilibrated resin (200 ml, Dowex AG50WX-8 (Na$^+$ form) was added and the reaction mixture was transferred to spin cups and into cup holders. The mixture was passed through the Dowex AG50WX-8 resin and the filtrate collected in a spin cup. NOS activity was determined by counting the radioactivity in the flow-through (unbound) fraction. Each assay was measured in triplicate.

Agmatinase Activity Assay

Agmatinase activity was measured by the method of Satishchandran and Boyle (1986) as detailed in Sastre et al. (1996). The assay is based on the hydrolysis of guanido [$^{14}$C]-agmatine to [$^{14}$C]-urea and putrescine, and subsequent trapping of [$^{14}$C]—CO$_2$ from the labeled urea, by the addition of urease. Assays were carried out for 30 minutes at 37° C. in 300 µl of sample containing 100 mM HEPES, pH 7.8, 4 mM MgSO$_4$, 1 mM dithiothreitol, 10 mM L-agmatine, 7 µM [$^{14}$C]-agmatine and 0.06 units of urease. Release of [$^{14}$C]—CO$_2$ from [$^{14}$C]-urea was measured by trapping the [$^{14}$C]—CO$_2$ in filter paper wicks saturated with benzethonium hydroxide. The reaction was stopped by injection of 40% trichloroacetic acid into the reaction chamber and the filters transferred to mini-vials containing 5 mL CYTOS-CINT® cocktail (ICN Biomedicals), and counted for radioactivity by liquid scintillation spectrometry using a Beckman model LS 5801 scintillation counter.

Arginine Decarboxylase (ADC) Activity Assay

The activity of ADC was measured in cell membrane fractions as described in Li et al. (1994), and is based on the release of [$^{14}$C]O$_2$ from [1-$^{14}$C]Arginine. Cell pellets were resuspended in Tris-HCl, EDTA (ethylene diamine tetracetic acid) buffer (pH7.4), sonicated, and centrifuged at 27,000× gravity for 20 minutes. The membrane pellet was washed once by sonication and recentrifugation in Tris-HCl buffer and resuspended in the incubation buffer. The membrane suspension (500 µl) was incubated for 1 hour at 25° C. in 20 mM Tris-HCl buffer (pH 8.25), containing 1 mM MgSO$_4$, 0.5 mM dithiothreitol, 0.5 mM PMSF (phenylmethylsulfonyl fluoride), 0.2 mM EDTA, 0.1 mM L-arginine, and 7.28 µM L-[1-$^{14}$C]arginine. Release of [$^{14}$C]O$_2$ in filter-paper wicks saturated with benzenthonium hydroxide. The reaction was stopped by the injection of 40% TCA (trichloroacetic acid) into the reaction chamber, the filters were transferred to minivials containing 5 mL CYTOSCINT® cocktail (ICN Biomedicals), and counted for radioactivity by liquid scintillation spectrometry.

[$^3$H]-MK801 Binding Assay

The binding of [$^3$H]-MK801 to NMDA (N-methyl-D-aspartate) receptors was measured in rat brain membranes as described in Renolds et al. (1990). Briefly, the membranes were incubated in HEPES buffer (pH 7.4) containing 0.4 nM [$^3$H]-MK801, 100 µM glutamate, and 30 µM glycine for 1 hour at 25° C. The binding was terminated by rapid filtration over glass fiber filters and radioactivity counted. Nonspecific binding was defined using 50 µM unlabelled MK801.

Determination of Quantitative Structure-Activity Relationships (QSAR)

QSAR were studied by ab initio Hartree-Fock calculations with the Gaussian 94 computer program (Frisch et al. 1995). Based on the optimized geometry and van der Waals radius of each atom, calculations were performed with BlogP and BlogW programs (Bodor et al. 1989, 1992A, and 1992B) to determine molecular surfaces, volumes, ovalities, partition coefficients, and water solubilities. Linear combinations of these calculated descriptors were then fitted to the observed enzyme activities. The observed activities were the remaining percentage of rat agmatinase activity at 0.5 mM of each compound, the remaining percentage of rat NOS isozyme activity at 1 mM of each compound, and the remaining percentage of rat brain NMDA receptor binding at 0.1 mM of each compound.

Results

Fourteen agmatine analogues (FIG. 1) were tested for inhibition of rat agmatinase, ADC, NOS isozymes, and the NMDA receptor. Data for inhibition of rat agmatinase, rat NOS isoforms, and competitive binding at the rat brain NMDA receptor are listed in Tables 1, 2, and 3, respectively. From the tested 14 compounds, no single compound was found with pure selectivity as a mammalian agmatinase inhibitor (i.e. that did not also inhibit, to some degree, the NOS isozymes and/or the NMDA receptor). However, none of the compounds inhibited mammalian ADC (arginine decarboxylase) to a detectable degree (note: the experiments with CS51 were not interpretable for ADC and agmatinase).

Figure 2:
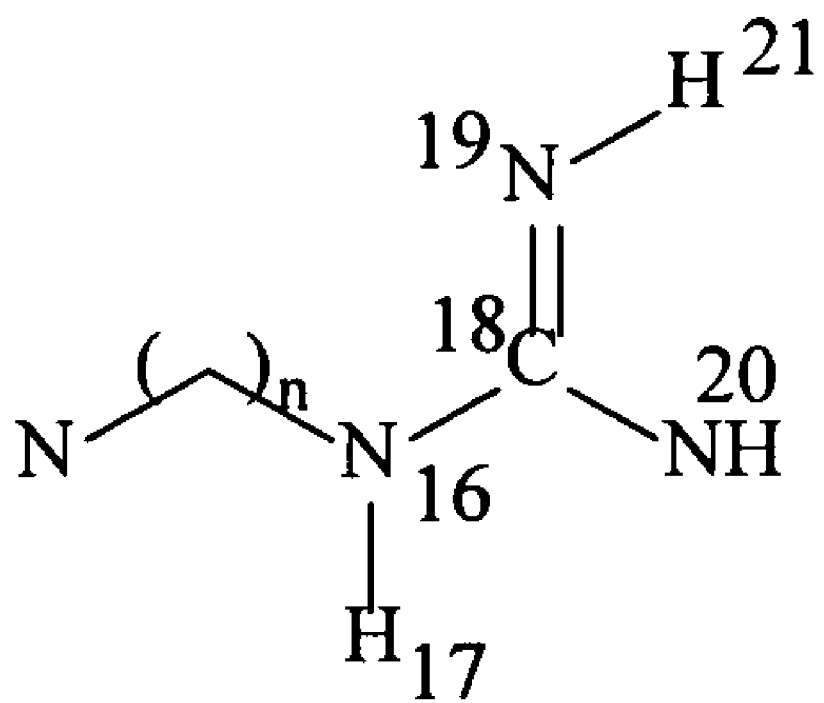

QSAR analysis of the guanidine group in each compound provides certain predictions about the types of compounds that are likely to be selective for agmatinase. The atom numbering scheme of the guanidine group used herein is shown FIG. 2. For the present experiments, the equation providing the best correlation for activity remaining (AR) (i.e. percentage of activity not inhibited) of rat agmatinase was:

$$AR = 0.3225D + 72.76D1916 + 64.97D1920 - 192.58H21 - 253.09 (n=12, F=6.8033, r=0.8919, SD=0.13199)$$ 
EQUATION 1

Where "n" is the number of compounds contributing to the regression; "r" is the correlation coefficient; "SD" is the standard deviation; and "F" is the Fisher's variance ratio. The "D" in the equation is the calculated dipole moment of the compound. "D1916" and "D1920" are the distances between N19 and N16 and between N19 and N20, respectively, and H21 is the charge on the H21 (see FIG. 2).

Figure 4:
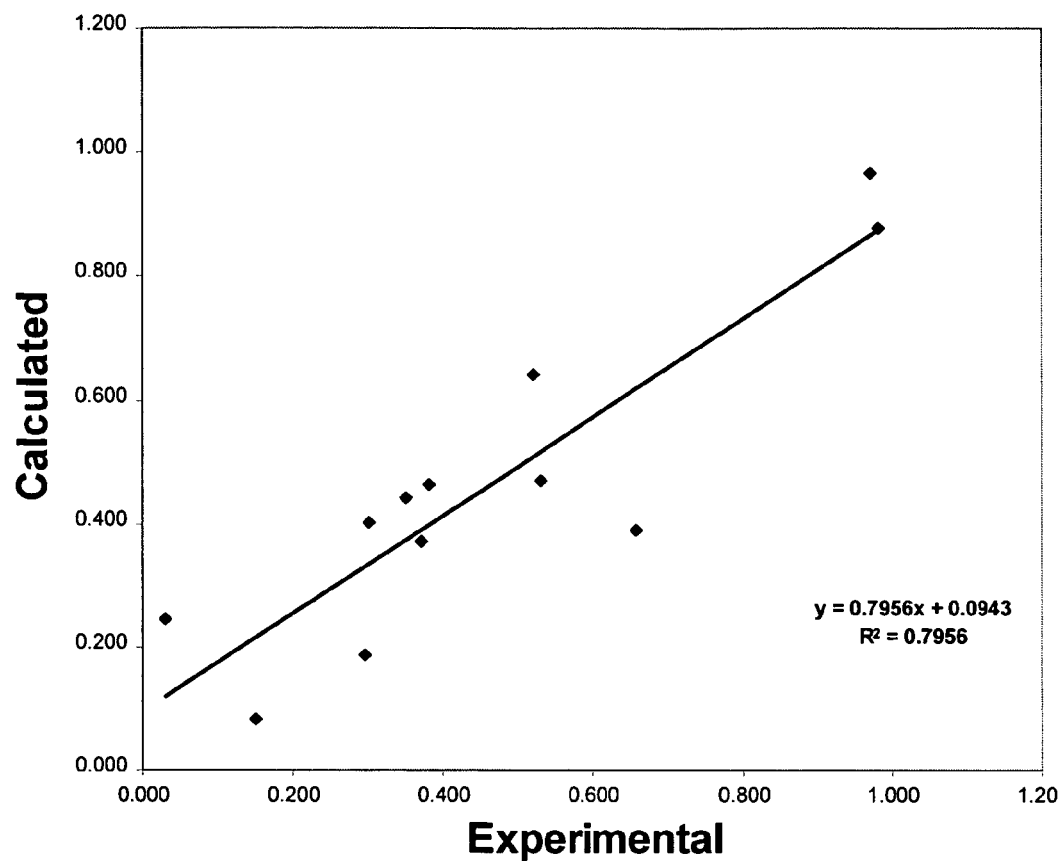

The experimental and calculated (in accordance with Equation 1) of the activities of the analogues on rat agmatinase are shown in FIG. 4. This QSAR analysis indicates that the smaller the dipole moment, the smaller the N19 and N16 distance, and the smaller the N19 and N20 distance, and the greater the charge on the H21, the more potent the compound is at inhibiting agmatinase.

TABLE 1

Results for Inhibition by Agmatine Analogues of Rat Agmatinase

|  | Compounds | Agmatinase activity remaining (%) (Conc = 0.5 mM) |
|---|---|---|
| 1 | Agmatine sulfate | 37% |
| 2 | Amino guanidine | 53% |
| 3 | Arcaine sulfate | 29.5% |
| 4 | 3-Aminopropylguanidine | 3.1% |
| 5 | Trans-4-Aminocyclohexy guanidine | 97.0% |
| 6 | Alpha-Vinylarginine | 52.0% |
| 7 | CS51 | Not interpretable* |
| 8 | R74 | 15.3% |
| 9 | TRV187 | 66.0% |
| 10 | TRV162 | 98.0% |

TABLE 1-continued

Results for Inhibition by Agmatine Analogues of Rat Agmatinase

| | Compounds | Agmatinase activity remaining (%) (Conc = 0.5 mM) |
|---|---|---|
| 11 | G3 | 35.0% |
| 12 | RO5 | 30.0% |
| 13 | Bis (3-(N-Iminomethyl)-aminopropyl)amine | 38.0% |

*Methanol had to be used to solubilize CS51, and even the lowest concentration of methanol in the assay was inhibitory by itself.

QSAR calculations similar to those for agmatinase were performed for nNOS. For the nNOS experiments, the equation providing the best correlation for activity remaining (AR) (i.e. percentage of activity not inhibited) of rat nNOS was:

$$AR=0.0882DNN19-99.890D1921+26.073D1620+40.970 (n=13, F=18.1157, r=0.9262, SD=0.10607).\quad \text{EQUATION 2}$$

Where "n" is the number of compounds contributing to the regression; "r" is the correlation coefficient; "SD" is the standard deviation; and "F" is the Fisher's variance ratio. The "DNN19" D1921, and D1620 are the distances between "N" (the unlabeled nitrogen atom in FIG. 2) and N19, between N19 and H21, and between N16 and N20, respectively.

Figure 5:
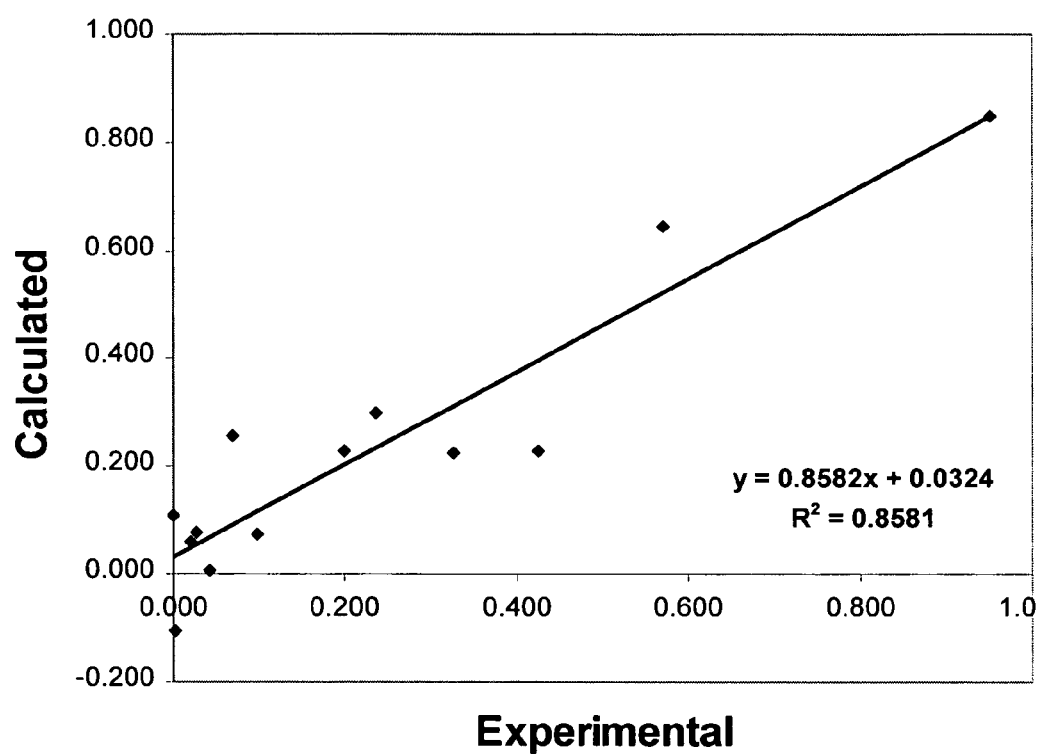

The experimental and calculated (in accordance with Equation 2) of the activities of the analogues on rat nNOS are shown in FIG. 5. These data indicate that more potent nNOS inhibitors have a greater the distance between the unlabeled nitrogen atom in FIG. 2 and N19, a greater the distance between N19 and H21, and a smaller distance between N16 and N20.

Similar QSAR calculations were performed for iNOS. For the iNOS experiments, the equation providing the best correlation for activity remaining (AR) (i.e. percentage of activity not inhibited) of rat iNOS was:

$$AR=17.559LUMO+165.71D1921+0.039287V-13.152O-155.38 (n=13, F=13.7018, r=0.9341, SD=0.13612).\quad \text{EQUATION 3}$$

Where "n" is the number of compounds contributing to the regression; "r" is the correlation coefficient; "SD" is the standard deviation; and "F" is the Fisher's variance ratio; where "LUMO" is the lowest unoccupied molecular orbital energy, "D1921" is the bond length of N19 and H21, "V" is the volume of the compound and "O" is the ovality of the compound.

Figure 6:
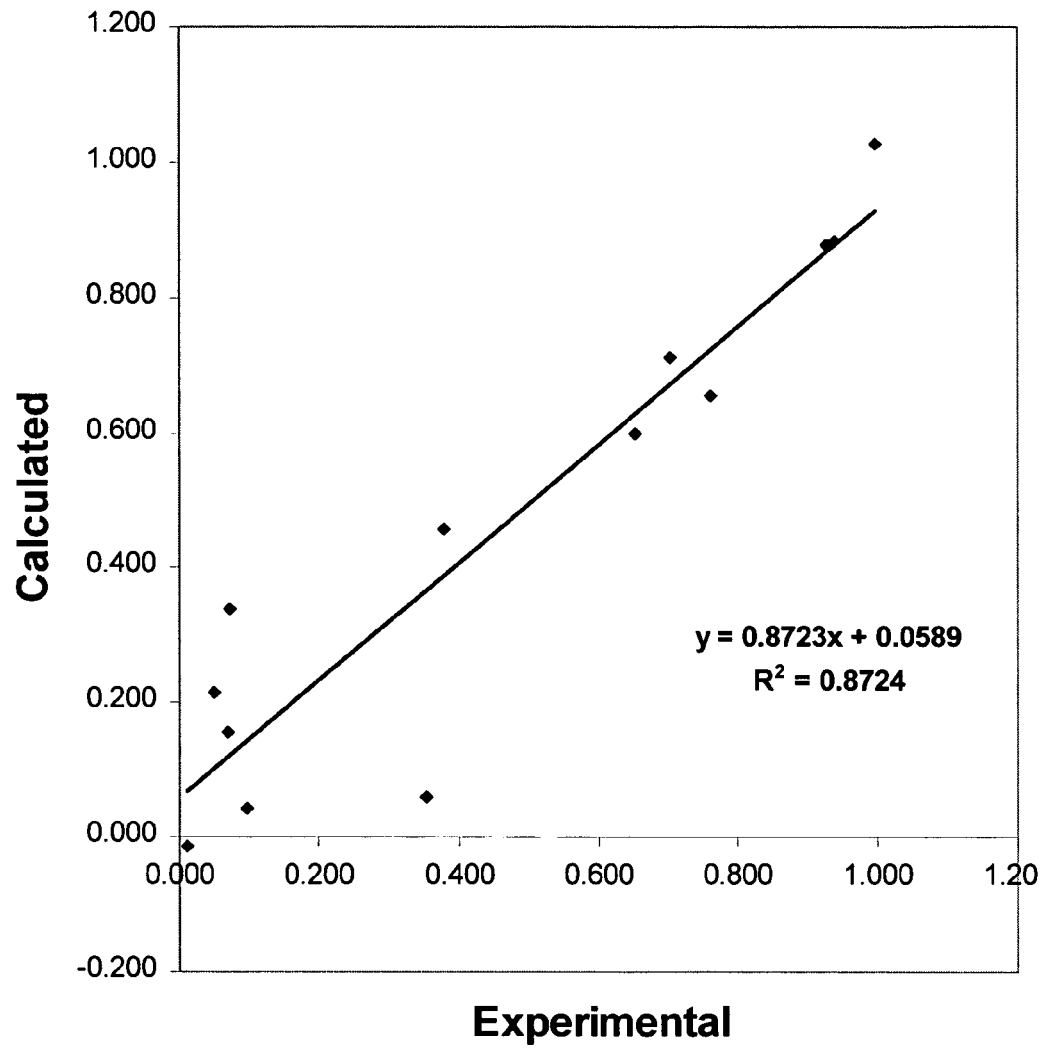

The experimental and calculated (in accordance with Equation 3) of the activities of the analogues on rat iNOS are shown in FIG. 6. These data indicate that more potent iNOS inhibitors have lower LUMO energy, a smaller N19 to H21 bond length, a smaller molecular volume, and a higher ovality value.

Similar QSAR calculations were also performed for eNOS. For the eNOS experiments, the equation providing the best correlation for activity remaining (AR) (i.e. percentage of activity not inhibited) of rat eNOS was:

$$AR=41.468D1820+57.345N19-359.848D1617+351.56 (n=13, F=18.3879, r=0.9272, SD=0.12200).\quad \text{EQUATION 4}$$

Where "n" is the number of compounds contributing to the regression; "r" is the correlation coefficient; "SD" is the standard deviation; and "F" is the Fisher's variance ratio; where "D1820" and "D1617" are the distances between carbon-18 (C18) and N20 and between N16 and H17 respectively; and where "N19" is the charge on nitrogen-19.

Figure 7:
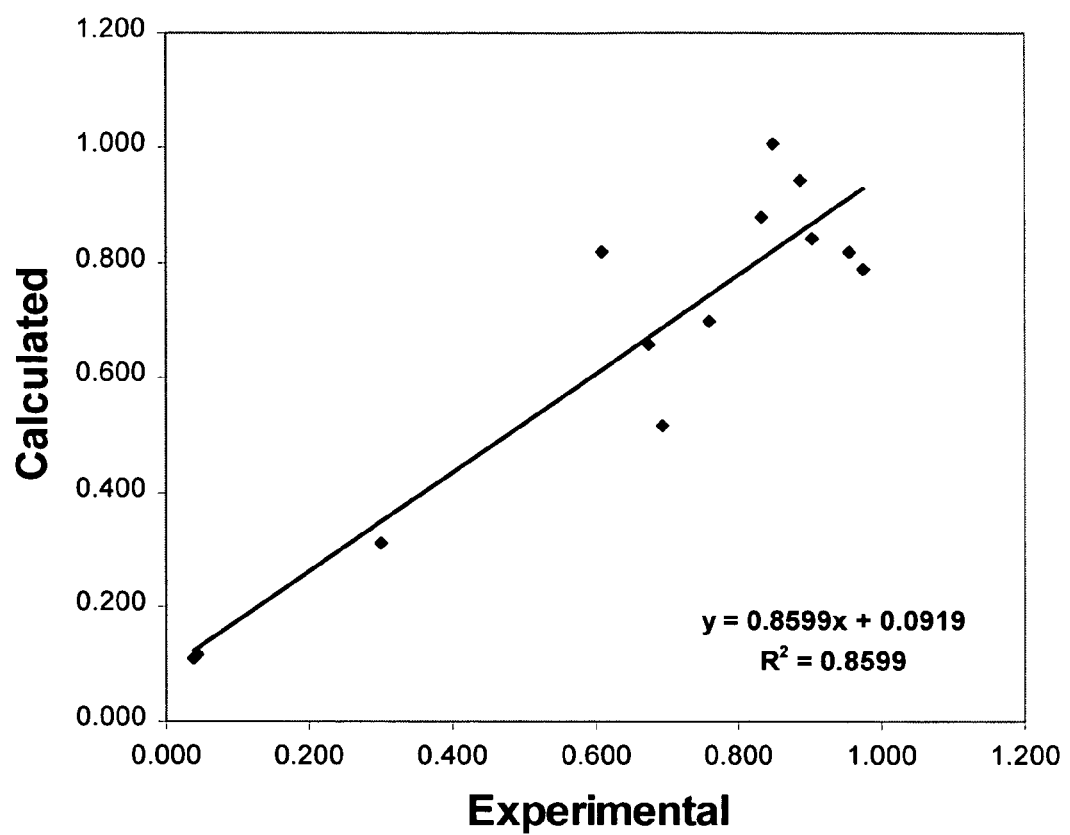

The experimental and calculated (in accordance with Equation 4) of the activities of the analogues on rat eNOS are shown in FIG. 7. These data indicate that more potent eNOS inhibitors have smaller distances between C18 and N20, a lower charge on N19, and greater distances between N16 and H17.

TABLE 2

Results for Rat NOS Inhibition by Agmatine Analogues

| | Compounds | Activity Remaining (%) (Conc = 1 mM) nNOS | Activity Remaining (%) (Conc = 1 mM) iNOS | Activity Remaining (%) (Conc = 1 mM) eNOS |
|---|---|---|---|---|
| 1 | Agmatine sulfate | 32.5 | 35.2 | 97.4 |
| 2 | Amino guanidine | 20.0 | 1.0 | 30.0 |
| 3 | Arcaine sulfate | 9.8 | 37.8 | 83.4 |
| 4 | 3-Aminopropylguanidin | 6.9 | 5.1 | 60.8 |
| 5 | Trans-4-aminocyclohexyl guanidine | 42.5 | 99.6 | 69.4 |
| 6 | Alpha-vinylarginine | 4.2 | 7.0 | 67.4 |
| 7 | CS51 | 95.0 | 94.0 | 84.9 |
| 8 | R74 | 2.1 | 9.6 | 90.5 |
| 9 | TRV187 | 2.6 | 70.2 | 75.9 |
| 10 | TRV162 | 57.0 | 92.7 | 95.6 |
| 11 | G3 | 0.1 | 7.2 | 3.9 |
| 12 | RO5 | 0.24 | 76.2 | 4.3 |
| 13 | Bis (3-(N-iminomethyl)-aminopropyl)amine | 23.5 | 65.2 | 88.7 |
| 14 | 7-nitroindazole | 1.0 | 1.0 | 0 |

QSAR calculations similar to those performed for agmatinase were also performed for the inhibition of NMDA receptor-binding. For the NMDA receptor-binding inhibition experiments, the equation providing the best correlation for binding remaining (AR) (i.e. percentage of binding not inhibited) for the rat NMDA receptor was:

$$AR=0.6715-0.2503 LOGP-0.3023 LOGW+ \\ 0.1970 DNN19-0.2873 DNN20 (n=13, \\ F=9.64147, r=0.9101, SD=0.07786).$$ EQUATION 5

Where "n" is the number of compounds contributing to the regression; "r" is the correlation coefficient; "SD" is the standard deviation; and "F" is the Fisher's variance ratio; where "LOGP" is the calculated logarithm of the partition coefficient of the compound, "LOGW" (logarithm of the water solubility, units of moles/liter) is the calculated log of the water solubility of the compound; and "DNN20" is the distance between the N and N20.

Figure 8:
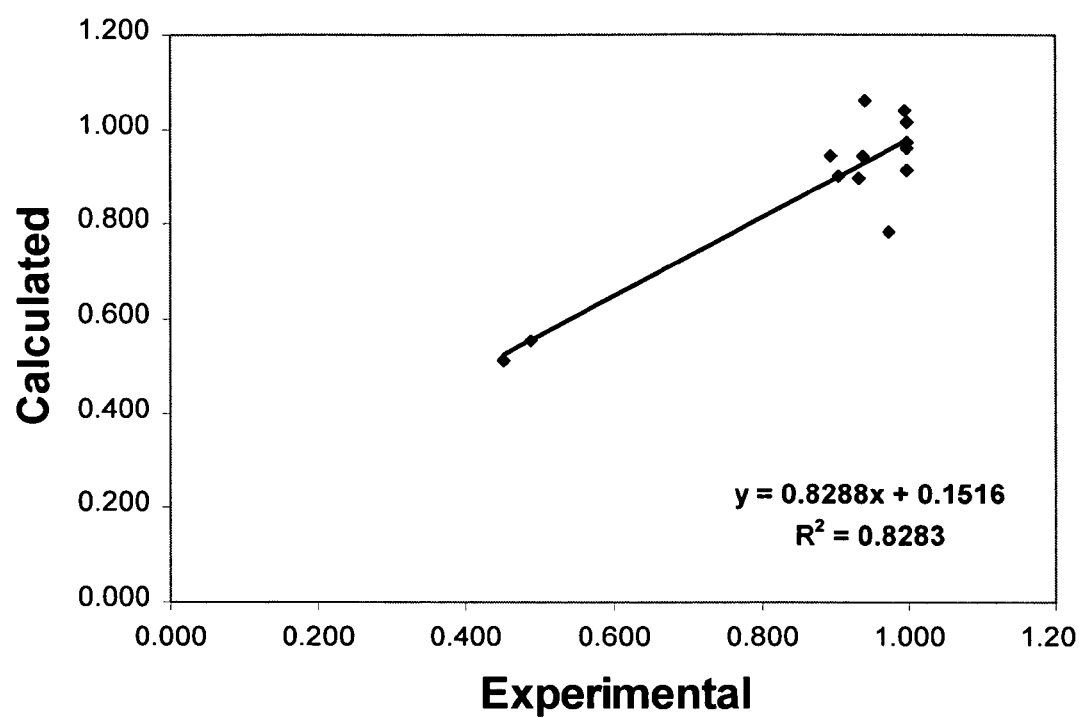

The experimental and calculated (in accordance with Equation 5) of the activities of the analogues on the rat NMDA receptor are shown in FIG. 8. These data indicate that compounds that are more potent rat NMDA binding inhibitors have greater partition coefficients, greater water solubility, greater distances between N and N20, and smaller distances between N and N19.

It is important to note that none of the compounds tested as part of the current invention showed any inhibitory effect on the activity of arginine decarboxylase (ADC). Thus, the compounds were to some degree agmatinase selective (i.e. they provided inhibition of agmatinase without inhibiting ADC).

TABLE 3

Results of Competitive Binding by Agmatine Analogues on Rat Brain NMDA Receptors Using [$^3$H]MK801

| | Compounds | $^3$H-: MK801 Binding Remaining (%) (Conc = 0.1 mM) |
|---|---|---|
| 1 | Agmatine sulfate | 93.8% |
| 2 | Amino guanidine | 90.6% |
| 3 | Arcaine sulfate | 45.1% |
| 4 | 3-Aminopropylguanidine | 93.9% |
| 5 | Trans-4-Aminocyclohexyl guanidine | 97.3% |
| 6 | Alpha-Vinylarginine | 99.7% |
| 7 | CS51 | 99.7% |
| 8 | R74 | 99.7% |
| 9 | TRV187 | 93.2% |
| 10 | TRV162 | 99.4% |
| 11 | G3 | 89.3% |
| 12 | RO5 | 48.9% |
| 13 | Bis (3-(N-Iminomethyl)-aminopropyl)amine | 99.7% |

None of the compounds examined for this example had absolute selectivity for mammalian agmatinase. Those compounds that effectively inhibited agmatinase also inhibited NOS isozymes. Nevertheless, the fact that QSAR predictions were distinct for each of the biological targets indicates that it is possible to synthesize compounds that are selective for and between mammalian agmatinase and ADC.

Building on the five QSAR correlations described above, the instant invention also provides mathematical equations that are useful as part of one embodiment of the invention to provide a means for predicting the activities of novel compounds. For example, with respect to agmatinase, the method provides a means for identifying those compounds that are best suited as agmatinase inhibitors or chemical leads to prepare such inhibitors.

For instance, analogues that have more compact N19-N16 and N19-N20 distances and a higher positive charge on H21 are predicted to be more effective as agmatinase inhibitors.

Those skilled in the art will appreciate that the compositions and/or methods disclosed and claimed herein can be made and executed without undue experimentation in light of the present disclosure. While the compositions and methods of this invention have been described in terms of preferred embodiments, it will also be apparent to those of skill in the art that variations may be applied to the compositions and in the steps or in the sequence of steps of the methods described herein without departing from the concept of the invention. Even more specifically, it will be apparent that certain compounds which are both chemically and physiologically related may be substituted for the compounds described and/or disclosed herein to achieve the same or similar results. All such similar substitutes and modifications apparent to those skilled in the art are deemed to be within the scope of the current invention.

REFERENCES

The following references, to the extent that they provide exemplary procedural or other details supplementary to those set forth herein, are specifically incorporated herein by reference.

Aricoioglu-Kartal, F. et al. (1997) "Inhibitory effect of agmatine on noloxone-precipitated abstinence syndrome in morphine dependent rats" Life Sci. 61:1775-81.

Bodor, N. et al. (1989) "A new method for estimation of partition coefficient" J. Am. Chem. Soc. 111:3783-86.

Bodor, N. et al. (1992A) "An extended version of a novel method for the estimation of partition coefficients" J. Pharm. Sci. 81:272-281.

Bodor, N. et al. (1992B) "A new method for the estimation of the aqueous solubility of organic compounds" J. Pharm. Sci. 81:954-960.

Bret, D. S. et al. (1990) "Isolation of nitric oxide synthetase, a calmodulin requiring enzyme" Proc. Natl. Acad. Sci. USA 87:682-685.

Carmignani, M. et al. (2001) "Novel hypotensive agents from Verbesina caracasana: synthesis and pharmacology of (3,4-dimethoxycinnamoyl)-N(1)-agmatine and synthetic analogues" J. Med. Chem. 44:2950-58.

Demady, D. R. et al. (2001) "Agmatine enhances the NADPH oxidase activity of neuronal NO synthase and leads to oxidative inactivation of the enzyme" Mol. Pharmacol. 59:24-29.

Demehri, S. et al. (2003) "Agmatine exerts anticonvulsant effect in mice: modulation by alpha(2)-adrenoceptors and nitric oxide", Neuropharm 45:534-542.

Fairbanks, C. A. et al. (2000) "Agmatine reverses pain induced by inflammation, neuropathy, and spinal cord injury", Proc. Natl. Acad. Sci. USA 97:10584-89.

Frisch, M. J. et al. (1995) Gaussian 94, Revision E.2., Gaussian, Inc., Pittsburgh Pa.

Gilad, G. M. et al. (1996) "Agmatine treatment is neuroprotective in rodent brain injury models" Life Sci. 58:41-46.

Kolesnikov, Y. et al. (1996) "Modulation of opioid analgesia by agmatine" Eur. J. Pharmacol. 296:17-22.

Lavinski, D. et al. (2003) "Agmatine induces anxiolysis in the elevated plus maze task in adult rats" Behav. Brain Res. 141:19-24.

Li, G. et al. (1994) "Agmatine: and endogenous clonidine-displacing substance in the brain", *Science* 263:966-969.

Li, J. et al. (1999) "Effects of agmatine on tolerance to and substance dependence on morphine in mice" *Chung Kuo Yao Li Hsuch Pao* 20:232-238.

Pedersen, M. L. et al. (1993) "Formal alpha-vinylation of amino acids: use of a new benzeneselenolate equivalent" *J. Org. Chem.* 58:6966-75.

Regunathan, S. et al. (2000) "Characterization of arginine decarboxylase in rat brain and liver: distinction from ornithine decarboxylase" *J. Neurochem.* 74:2201-2208.

Reis, D. J. et al. (2000) "Is agmatine a novel neurotransmitter in brain?", *Trends Pharmacol Sci.* 21:187-193.

Reynolds, I. J. et al. (1990) "Arcaine is a competitive antagonist of the polyamine site on the NMDA receptor" *Eur. J. Pharmacol.* 177:215-216.

Sastre, M. et al. (1996) "Agmatinase activity in rat brain: a metabolic pathway for the degradation of agmatine", *J. Neurochem.* 67:1761-65.

Yang, X. C. et al. (1999) "Agmatine selectively blocks the N-methyl-D-aspartate subclass of glutamate receptor channels in rat hippocampal neurons", *Pharmacol. Exp. Ther.* 288:544-549.

Zomkowski, A. D. et al. (2002) "Agmatine produces antidepressant-like effects in two models of depression in mice", *Neuroreport* 13:387-391.

What is claimed is:

1. A method of reducing agmatinase activity in an animal comprising administering to the animal an effective amount of a composition comprising one or a combination of two or more compounds selected from the compounds having the following structures:

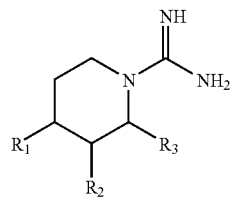 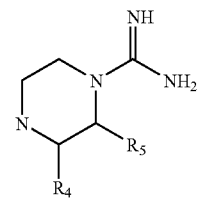

where $R_1$ is either —$NH_2$ or —H and where $R_2$, $R_3$, $R_4$, and $R_5$ are either —$CH_3$ or —H.

2. The method of claim 1 wherein the animal is a mammal.

3. The method of claim 1 wherein the animal is human.

* * * * *